United States Patent [19]

Lemonnier

[11] Patent Number: 4,465,501
[45] Date of Patent: Aug. 14, 1984

[54] APPARATUS FOR ASEPTIC AND ANTIPARTICULATE OPENING OF SEALED GLASS CONTAINERS

[75] Inventor: Jean Lemonnier, Le Vesinet, France

[73] Assignee: Millipore S.A., Molsheim, France

[21] Appl. No.: 438,666

[22] Filed: Nov. 2, 1982

[30] Foreign Application Priority Data

Nov. 5, 1981 [FR] France .................. 81 20734

[51] Int. Cl.³ ............................................. C03B 23/26
[52] U.S. Cl. ...................................... 65/285; 65/105; 65/113; 65/270; 65/271
[58] Field of Search ................ 65/105, 112, 113, 166, 65/271, 285, 270

[56] References Cited

U.S. PATENT DOCUMENTS

| | | |
|---|---|---|
| 2,224,486 | 12/1940 | Richter . |
| 2,704,418 | 3/1955 | Gerbaud . |
| 2,956,372 | 10/1960 | Madigan ............................ 65/113 X |
| 3,188,191 | 8/1965 | Farnsworth ......................... 65/113 |
| 3,375,948 | 4/1968 | Creevy et al. ...................... 65/105 X |
| 3,923,487 | 12/1975 | Lewis .................................... 65/110 |

FOREIGN PATENT DOCUMENTS

| | | |
|---|---|---|
| 2719684 | 3/1977 | Fed. Rep. of Germany . |
| 2290496 | 11/1975 | France . |
| 191581 | 12/1921 | United Kingdom . |
| 533473 | 11/1939 | United Kingdom . |

Primary Examiner—Arthur Kellogg
Attorney, Agent, or Firm—Karl W. Flocks; Sheridan Neimark

[57] ABSTRACT

According to the method of aseptic and antiparticulate opening of a sealed glass ampul, one end of the ampul is submitted to a powerful thermal flux produced by flame tongue generating sources on a very localized zone for a time period sufficient to obtain melting of the glass while maintaining the adjacent portion thereof at lower temperature for preserving its rigidity, such time period being the shorter the smaller that volume of gas contained in the ampul which is quickly brought to an increased temperature and pressure to cause the ampul to be opened up in the considered molten zone.

6 Claims, 10 Drawing Figures

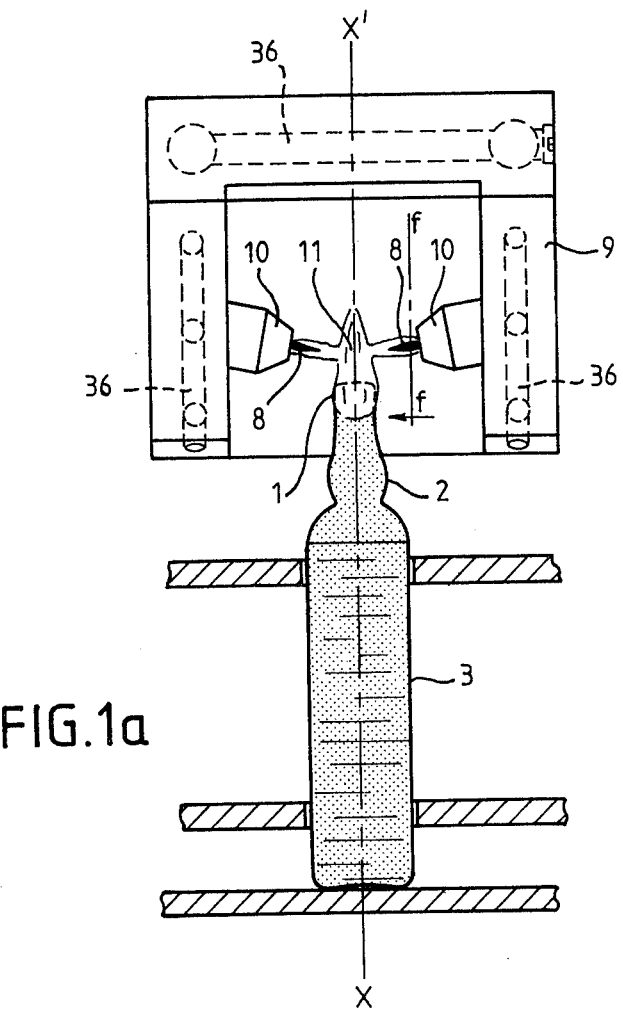
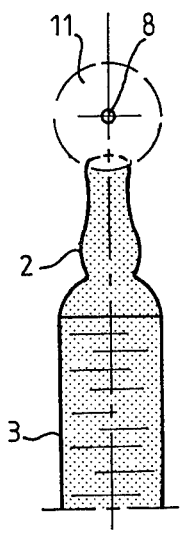
FIG.1a
FIG.1c
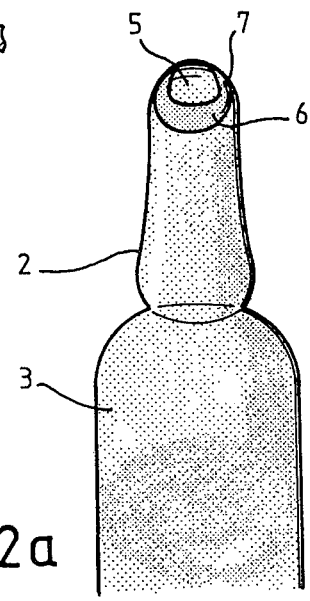
FIG.2a

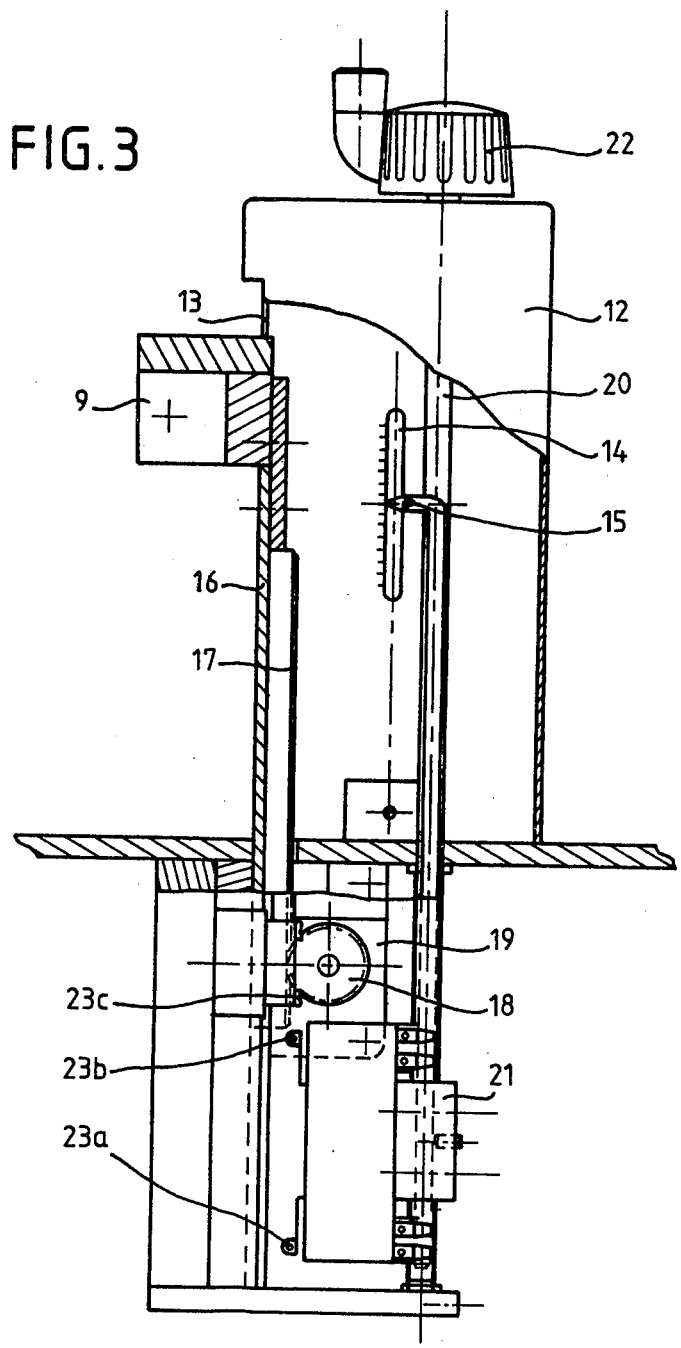

APPARATUS FOR ASEPTIC AND ANTIPARTICULATE OPENING OF SEALED GLASS CONTAINERS

This invention relates to a method of aseptically and antiparticulately opening sealed glass containers to permit in particular the contents of such containers to be checked for sterility. The invention also relates to the device and apparatus for carrying out such method.

As recommended by the various pharmacopoeias, any products and more especially any products intended for injection into the human body in the intravenous, intramuscular or parenteral manner must be submitted to sterility tests to check for the absence of microorganisms such as bacterias, mushrooms or moulds or even solid foreign matters.

It will be understood that during the testing of many product samples such as for example solutions, solutes, or even solid or powder products contained in ampuls, it is significant to operate under reliable aseptic conditions to prevent as much as possible any risks of false positives, and this mainly upon opening such containers or ampuls and during transfer of the products to the filtration system which is used to effect such testing.

Systems for opening such ampuls have been known, using mechanical means implying either filing through the neck of the ampul followed by a percussive action or sawing off the neck possibly followed by a heating and/or percussive action. This processing method not only runs the risk that the ampul should break outside the desired zone and that the product contained in it be poured unexpectedly, thereby becoming unusable for the sterility test, but also the risk of introduction of particles of contaminated glass into the medium to be submitted to such test. Such risk is the stronger because such mechanical means cause formation of dusts or thin glass splits that may easily reach and contaminate the product to be analyzed.

On the other hand, it is known to cause opening of an ampul by heating the glass at the points of lower strength of the neck without reaching the melting temperature thereof, such opening being realized by explosion caused by release of the air occluded in the glass heating zone. This processing method is disadvantageous in that the opening occurs in such zones of lesser strength, i.e. laterally and randomly and in that it then becomes uneasy to automatically introduce thereinto the needle of the hypodermic type which is used for taking the contents of the ampul.

On the other hand, proceeding until the glass is molten to make an opening therein along the longitudinal axis of the ampul to make it possible to introduce said hypodermic needle along such axis is also disadvantageous because of the risk of softening the glass in such a proportion that the orifice which is first produced closes itself by flowing out and deformation of molten glass of the lips of said orifice, on the one hand, and on the other hand, the risk of excessive heating of the contents of the ampul, resulting from the required prolonged heating to realize an appropriate orifice, such heating affecting gradually the ampul walls and directly or indirectly its contents.

As regards the possibility of drilling a glass ampul by means of a pointed tool brought to a very high temperature, it is easy to imagine the corresponding disadvantages such as splitting of glass by thermal stress and the risks resulting therefrom either relative to reliability or implenentation of the method.

This invention now provides a method of remedying these various deficiencies since it permits aseptic opening in a controlled and reproducible manner of glass ampuls while preventing any contamination or heating of the medium contained in such ampuls. It can be applied to any type of ampuls, it can be easily implemented, and utilized in a readily automatizable apparatus.

The method of this invention implies glass melting and it is substantially characterized by submitting one end of the glass ampul to a powerful thermal flux in a very localized zone for a sufficient time period to obtain melting of the glass therein while holding the adjacent planar or frusto-conical portion at a temperature lower than the melting temperature so as to preserve its rigidity, such period of time being the shorter, the smaller that volume of gas contained in the ampul which is brought quickly to an increased temperature and pressure, resulting in the opening of the ampul in the considered molten zone.

Advantageously, the extent of said localized zone lies in the neighbourhood of the longitudinal axis of the ampul to be opened.

The object of the invention is also a device for carrying out the method, which is itself characterized in that it comprises at least one heat source producing an intensive thermal flux in form of a flame tongue of a very high temperature close to the glass melting temperature, such flame tongue being directed so as to lie in a plane substantially tangent to the surface of the glass and adjacent to the longitudinal axis of the ampul.

According to one advantageous form of embodiment, such device can comprise two flame tongue producing sources facing each other and disposed so as to meet to form a substantially vertical disk like halo tangent to the surface of the glass to be treated.

According to an alternative form of embodiment, the device comprises more than two sources disposed to form a halo having a longitudinal axis substantially aligned with that of the ampul.

According to further characteristics:

the flame tongue generating source(s) are mounted on a fork which may be caused to move up and down to bring the flame tongue(s) and/or the halo to the desired relative position with respect to the surface of the glass to be treated.

The method and the device according to the invention can easily be utilized in an apparatus for testing sterility of products contained in sealed ampuls, such apparatus then comprising:

a station for opening the ampuls through glass melting, comprising the device as defined above;

means for transferring to said opening station the ampuls constituting the product samples to be tested;

an extraction station connected to a sterility testing device.

Such an apparatus according to the invention can be operable automatically, i.e. the ampuls to be opened will be successively opened, their contents taken out, and then admitted to the analyzing system proper.

To this end, the means for presenting ampuls to the opening station may consist of a sample carrier platen driven into a step by step feed motion which takes place only after opening an ampul and the extraction station may consist of a needle carrier device driven into an ascending and descending motion acting synchronously with the ascending-descending motion of the opening station device, on the one hand, and on the other hand, with the step by step motion of the sample carrier platen, said extraction station being itself connected to the sterility test apparatus having a suction device which in its turn is actuated synchronously with the ascending and descending motions of the needle carrier device.

The apparatus for carrying out the method and using the opening device according to the invention then comprises a control housing and means associated therewith, said housing and means being of a known type for enabling motions of each of the constituents of the apparatus to be synchronized with one another.

According to one characteristic the apparatus can comprise at the sample extraction station associated with the needle carrier device, a sterility checking device such as that described in French patent No. 7533838 (published under No. 2 290 496).

Other characteristics and advantages of this invention will appear more clearly from the following description which is made in the light of the attached drawings on which:

FIGS. 1a and 1b are schematic views for illustrating the method of this invention;

FIGS. 1c and 1d are corresponding partial views along the arrows f—f;

FIGS. 2a and 2b show ampuls being opened according to the invention;

FIG. 3 is an elevational view partly in cross-section of a device for carrying out the method of this invention;

With reference to these figures, the method of the invention consists of bringing to the molten state a very limited zone of a glass ampul, exclusive of the surrounding zones, which are themselves brought only to a temperature lower than the glass melting temperature. In the exemplifying form of embodiment illustrated in FIGS. 1a and 1b, the upper end or pole of the cap 1 terminating the neck 2 of the ampul 3 or its lower basis 4 is brought to the glass melting temperature.

The pressure of the air volume which has been heated in this manner then exerts itself upon such zone which is thus rendered more frangible, whereby the glass is pierced through at that point by violent escape of the air without deforming the surrounding zones. As a matter of fact, in the absence of thermal stress on such surrounding zones, which are themselves brought to a high temperature without however reaching the melting temperature, such zones have not the tendency of breaking up in an uncontrolled manner, on the one hand, and on the other hand, of flowing out so as to close off the so produced orifice due to the fact that they have not been brought to the molten state which would otherwise have permitted such flowing out.

Figure 2B:
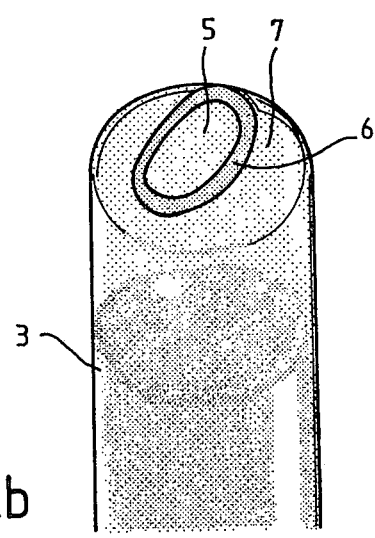

It is therefore advantageous for correctly carrying out the method, to effect melting of glass on a narrow surface in as short a period of time as possible to prevent the glass from being brought to the molten state progressively nearer on too large a surface thereby resulting in glass deformation and also deformation of the lips of the orifice made out and even, obturation of such orifice. It will therefore be understood that it is necessary to submit the zone to be caused to melt to a high temperature at least equal to the glass melting temperature such that a small volume of air occluded therein is brought to a temperature such that the resulting pressure exerts itself as quickly as possible upon that glass zone rendered frangible by melting. FIGS. 2a–2b show the result obtained by this method. It can be actually seen in these figures the orifices 5 made at the end of ampuls 3. The bulge 6 forms the lips thereof. It results from the violent escape of hot gases accluded therein the consequence of which was only to fold up and spread molten glass onto and over the surrounding zone 7 which remains unchanged and underwent no thermal stress.

To obtain this result, the device according to the invention for carrying out the method comprises at least a source for producing a flame taking the form of a very narrow tongue directed so as to "skim over" the zone in which the orifice must be made.

Figure 1B:
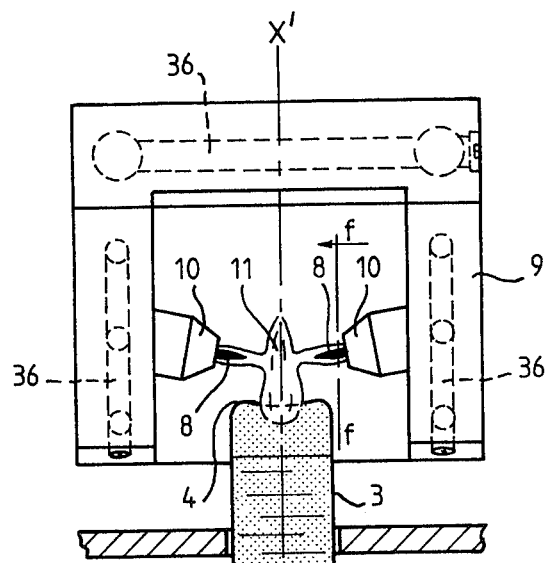
Figure 1D:
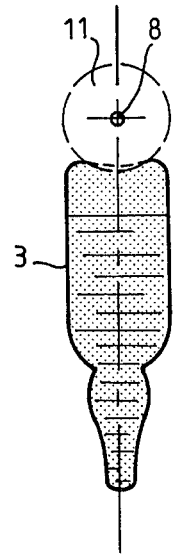

FIGS. 1a and 1b show an assembly in form of a stirrup 9 carrying on both of its opposite branches two nozzles or injectors 10, each connected to a source of a gas or a combustible gas mixture, not shown, with the diameter of such nozzles being selected so as to realize both flames tongues 8 the ends of which meet to form a disk like substantially vertical halo 11 tangent to the surface of the glass to be pierced.

As can be seen from these figures, the halo in which there is the highest temperature suitable for causing the glass to melt does not affect the pole of the cap of the ampul neck or the basis thereof on a narrow zone, the surrounding zones being submitted only to a lower temperature and consequently, not being submitted to the melting effect.

Depending on the inclination of the halo resulting from variations of the inclination of the flame tongues or the gas flow rate, in one or the other of the injectors, the orifice can be realized in an advantageous point in the neighbourhood of, or as close as possible to, the longitudinal axis X—X' of the ampul to facilitate best the operations for taking out the contents thereof.

In the event that the orifice must be formed in the bottom 4 of an ampul, the result obtained according to the invention is illustrated in FIG. 2b.

Analysis of such result immediately leads to the following remarks:

(a) With this method, it is possible to form orifices in glass ampuls in the immediate neighbourhood of their longitudinal axis in a controlled and reproducible manner, and also aseptically, due to the absence of any cause for pollution, or of introduction of foreign matters.

(b) The air occluded in such ampuls is heated in a relatively small volume thereby sheltering the contents of the ampuls from any excessive heating and consequently from any alteration that might be caused by thermal variations.

(c) Due to the location of the formed orifice, a needle for extraction of contents of an ampul can be easily and vertically inserted thereinto.

Figures 5A, 5B:
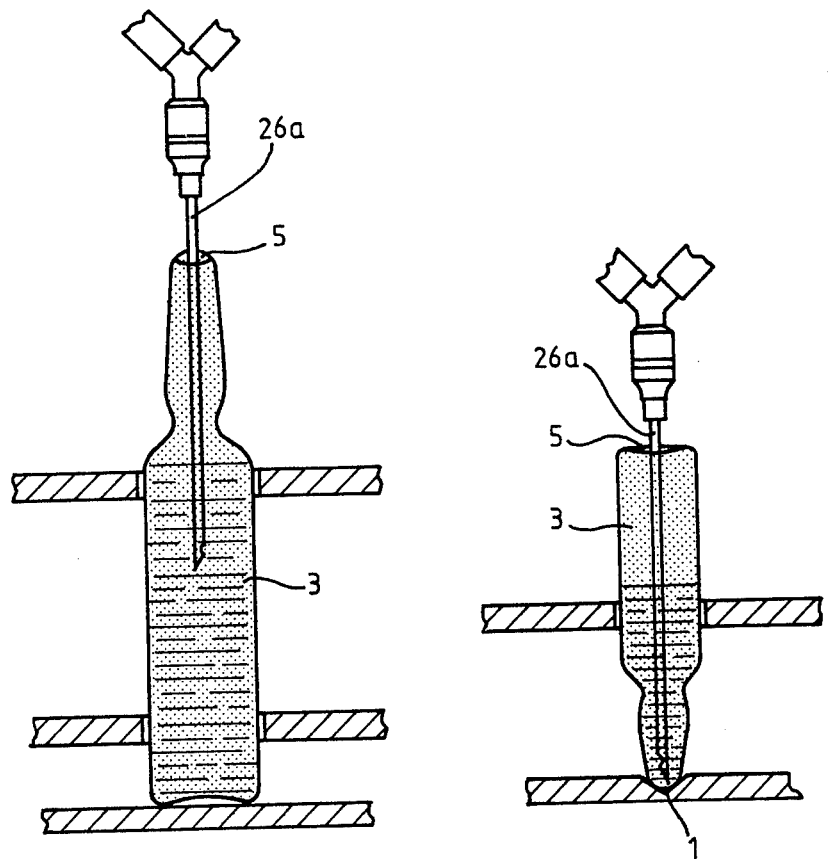
FIGS. 5a and 5b show the advantages that can be obtained by carrying out the method of the invention with ampuls of different capacities.

(d) Since an axial orifice can be made both in the neck and the bottom of an ampul, extraction of the ampul contents can be effected both in the standing position (see FIG. 5a showing an ampul of more than 1 ml from which the desired volume of solute can be extracted) and in the upside down position (see FIG. 5b showing an ampul of less than 1 ml from which all the solute must be taken out).

In view of the advantages and the progress of the method and device according to the invention, they can be utilized for realizing an apparatus suitable for use in an automatic assembly intended for aseptic extraction of ampul contents to check sterility thereof.

Such an apparatus is shown in FIG. 3. It is essentially constituted by a cylindric part 12 formed with a window 13 in which the stirrup 9 carrying the nozzles 10 and mentioned above is slidable as will be shown hereinafter. Moreover, along a generatrix of such cylindric part there is made a longitudinal slot 14 therein having a graduation scale in front of which a slide 15 can move in a manner such as described hereinafter and the function of which will also appear in the following description.

The stirrup 9 is carried by a plate 16 made integral with a rack 17 meshing with gear means 18 drivable into rotation by any suitable means such as e.g. an electric motor 19.

The index or slide 15 is mounted by a nut 21 to a shaft 20 the rotation of which can be controlled by a handle knob 22 to bring said slide to the desired position opposite the selected graduation in the graduated scale of slot 14. Such position controls the amplitude of the ascending-descending motions of the stirrup 9 for example through an electric connection being made by contacts 23a, 23b, 23c provided on the lower portion of the rack carrying part and the index carrying part to electrically control the motor 19 and therefore rotation of gear means 18 meshing with the rack 17.

Figure 4:
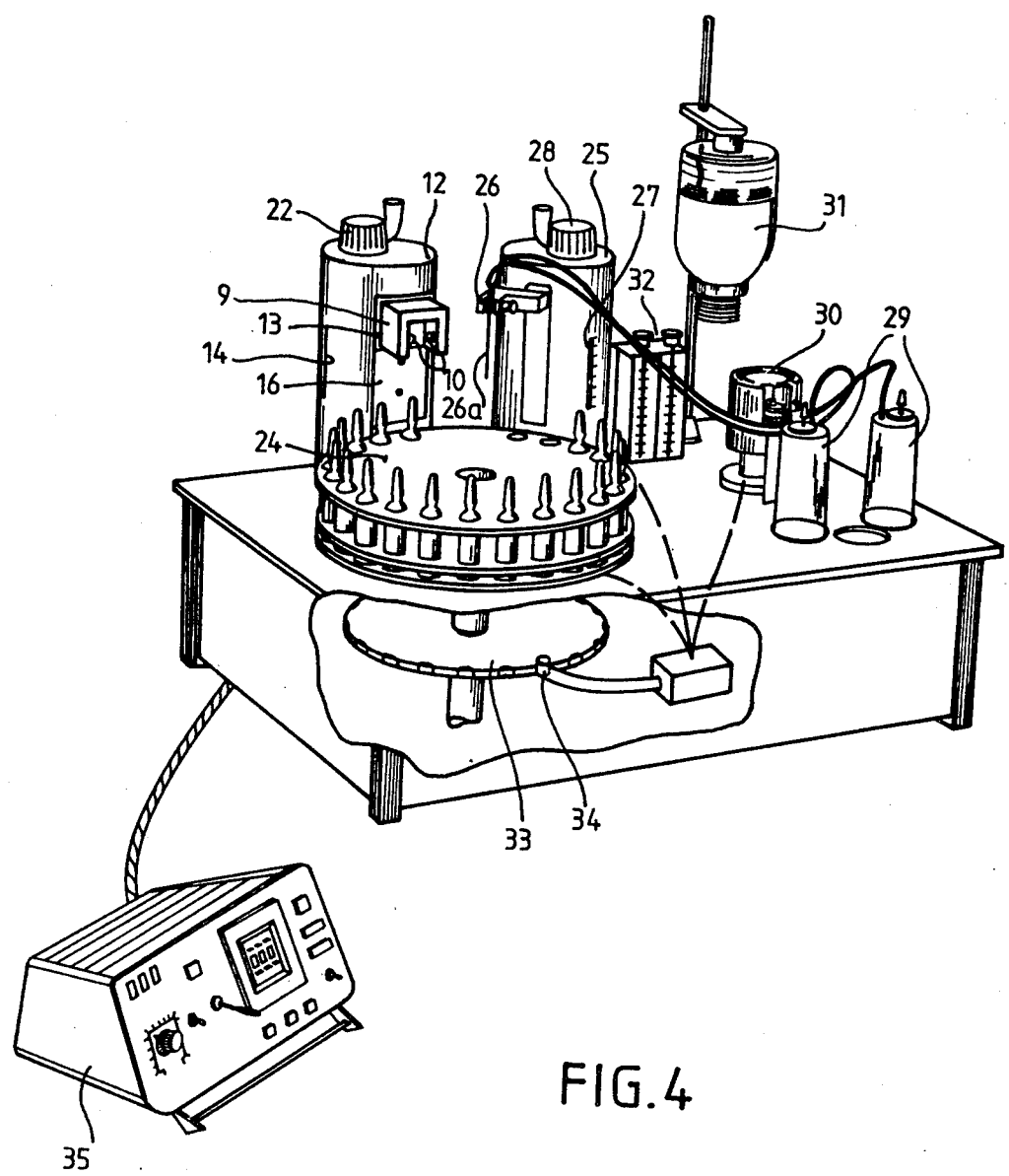
FIG. 4 is a perspective view of an exemplifying form of embodiment of an assembly of an automatic apparatus for carrying out the method and using the opening device according to the invention as applied to the testing of sterility in ampuls of solutes.

Such an apparatus can be used as mentioned above in an entirely automatic assembly shown in FIG. 4 so as to make a sterility test.

The assembly essentially comprises the ampul opening station 12 such as just described above, cooperating with a device for presenting the ampuls to be opened. The latter may consist e.g. of an ampul carrier platen 24 drivable into a step by step rotary motion as will be shown hereinafter. The height of the ampuls to be opened determines the height at which the stirrup carrying the generator of thermal flux lies so as to carry out the above defined method of the invention.

The assembly also comprises a station for extracting the contents of each ampul associated with said opening station, the extraction station consisting of a cylindric member 25 of the same structure and function as those of member 12, save for the fact that the stirrup carrying the generators of thermal flux is replaced with a hypodermic needle carrier 26—26a drivable into an ascending-descending motion the amplitude of which is controlled as above through a slide brought in front of a graduated scale 27 by the handle knob 28, depending on the depth of penetration of the needle within an opened ampul. The hypodermic needle 26a is directly connected to the apparatus for checking sterility. The latter can be of any suitable known type. It will be advantageously of the type described in French patent No. 7533838, i.e. comprising its two special boxes 29 which will not be described herein and one of which has been shown as directly connected to the hypodermic needle, on the one hand, and on the other hand, to the suction pump 30. At 31 there is also shown a reservoir for the appropriate liquid which is used for checking for sterility and it is not necessary to describe it again herein.

In FIG. 4 there are also shown two flowmeters 32 to permit control of the flow rate of the gas or combustible mixture feeding the station for opening the ampuls.

The means for realizing automatization of the assembly are within the knowledge of the man of the art and therefore will not be discussed herein; the automatization is obtained as follows:

The platen 24 is driven into rotation step by step by means of a disk 33 mounted on the same shaft, controlled by a motor (not shown) and comprising on its periphery a toothed portion of ratchet wheel type meshing with a contacting pawl 34 to control the downward or upward motion of the stirrup 9, the upward or donward motion of the needle carrier 26 and the start of the suction pump 30.

A housing 35 is provided for the control and the overall monitoring of the assembly to ensure proper operation thereof.

Thus, a sterility test cycle on a sample of the product contained in an ampul comprises the following tests:

(a) Presentation of an ampul to the opening station; stopping the platen 24 when a sealed ampul moves to the proper position with respect to the stirrup 9;

(b) Moving down the stirrup to the proper level above the ampul and action of the thermal flux according to the method of the invention; opening of the ampul;

(c) Feeding the disk until the so opened ampul lies in the proper position in respect to the hypodermic needle of the extraction station 25; during the same period of time the stirrup 9 is moved up again to be ready for the next step;

(d) Stopping the disk 24, moving down the hypodermic needle within the opened ampul, suction action of the pump 30 and entering the product at 29; during the same period of time, opening the following ampul, and the cycle is continued.

The electric devices and circuits for controlling such cycle are of the usual type and can be realized in a suitable manner known in itself.

To prevent excessive heating of the stirrup in the opening station, the stirrup 9 may comprise cooling circuit means produced by fluid circulation within its branches, such circuit means being designated by reference numeral 36. For the sake of clarity and simplification of the drawing the circuit for feeding gas or combustible gas mixture was not shown either.

The invention can obviously be applied for checking sterility of dry products (soluble or lyophilized powders). In that case a product solubilization station is provided between the opening station and the extraction station.

It will be understood that this invention was only described in a purely explanatory and not at all limitative way and that any useful modifications can be brought thereto without departing from its scope as defined in the appended claims.

I claim:

1. A device adapted to aseptically and antiparticulately open a sealed glass ampul containing a liquid or a solid product by melting the glass at the side of the desired opening while protecting said liquid or solid product from a temperature increase, said device comprising
    at least two heat sources for generating an intensive thermal flux in the form of flame tongues of a very high temperature close to the glass melting temperature, said heat sources facing each other and being disposed so that the flame tongues meet to form a substantially vertical disk-like halo tangential to the surface of said side of glass surface; and said at least two heat sources being mounted on a fork, said fork comprising cooling means for preventing overheating thereof.

2. A device according to claim 1, comprising more than two sources disposed so that the halo formed has a longitudinal axis substantially aligned with that of the ampul.

3. A device according to claim 1, wherein said fork is adapted to undergo an ascending-descending motion to bring the flame tongues or the halo to the relative desired position with respect to the surface of the glass to be treated.

4. An apparatus for testing sterility of products contained in sealed ampuls comprising:

a device according to claim 1 for opening the ampuls;
means for presenting to said opening device ampuls constituting samples of products to be tested;
an extraction station for extracting the contents of the ampul presented and opened; and
means for testing sterility of such contents.

5. The apparatus of claim 4 having automatized operation, wherein said means for presenting ampuls to the opening device comprises a sample carrier platen driven into a step-by-step feed motion which takes place only after an ampul is opened, and said extraction station comprises a needle carrier device driven into an ascending-descending motion acting synchronously with an ascending-descending motion of said opening device, on the one hand, and on the other hand, the step-by-step motion of said sample carrier platen, said apparatus further comprising a suction device itself actuated synchronously with the ascending-descending motions of said needle carrier device.

6. A device according to claim 5, wherein said automatized operation apparatus further comprises a control box and means associated therewith for synchronizing the motions of the carrier platen, needle carrier device, and suction device.

* * * * *